United States Patent [19]

Ditmore, Jr.

[11] 4,150,782

[45] Apr. 24, 1979

[54] DATA PROCESSING SYSTEM

[76] Inventor: Harry B. Ditmore, Jr., 4321 SW. Washouga, Portland, Oreg. 97201

[21] Appl. No.: 776,560

[22] Filed: Mar. 10, 1977

Related U.S. Application Data

[63] Continuation of Ser. No. 532,439, Dec. 13, 1974, which is a continuation of Ser. No. 385,153, Aug. 2, 1973.

[51] Int. Cl.² .......................... G06K 7/10; G06F 5/00; G09B 23/28
[52] U.S. Cl. ............................... 235/455; 35/17; 235/310; 250/566
[58] Field of Search ................ 235/151.3, 152, 154, 235/61.11 E, 61.12 R, 61.6 N, 61.6 A, 61.7 R, 454, 455; 35/8 R, 9 A, 17, 12; 340/347; 250/557, 566, 569

[56] References Cited

U.S. PATENT DOCUMENTS

| 1,526,717 | 2/1925 | Nunez | 35/17 |
|---|---|---|---|
| 1,988,634 | 1/1935 | Stonecypher | 35/12 |
| 2,605,965 | 8/1952 | Shepherd | 235/61.6 A |
| 2,795,705 | 6/1957 | Rabinow | 250/566 |
| 3,171,021 | 2/1965 | Jonker | 235/61.12 N |
| 3,188,907 | 6/1965 | Trampel | 340/173 LM |
| 3,215,848 | 11/1965 | Zworykin | 250/557 |
| 3,402,285 | 9/1968 | Wang | 235/154 |
| 3,610,901 | 10/1971 | Lynch | 235/152 |

Primary Examiner—Robert M. Kilgore
Attorney, Agent, or Firm—Jay M. Cantor

[57] ABSTRACT

A record is prepared recording certain findings to provide an object record. The information of the object record is compared with stored information which comprises a function of the probability of occurrence of these certain findings in a particular class. An index of matching is established between the stored information relating to the class and the information of the object record to provide readout information.

26 Claims, 21 Drawing Figures

TABLE 1
(ASSUMED PROBABILITIES OF
SYMPTOMS OF GASTROENTERITIS)

$$P(F_i|D_1D_2) = P(F_i|D_1) + P(F_i|D_2)[1 - P(F_i|D_1)]$$
$$\text{Log } P(F_i|D_1 D_2) = \text{Log}\{P(F_i|D_1) + P(F_i|D_2)[1 - P(F_i|D_1)]\}$$
AND
$$P(\bar{F_i}|D_1D_2) \; P(\bar{F_i}|D_1)[1 - P(F_i|D_1)]$$
$$\text{Log } P(\bar{F_i}|D_1D_2) \; \text{Log}[P(\bar{F_i}|D_2)] + \text{Log}[1 - (P\,F_i|D_1)]$$
$$= \text{Log}[P(\bar{F_i}|D_2)] + \text{Log}[P(\bar{F_i}|D_1)]$$

NOTE: AREA ABCD = AREA DXYZ

DATA PROCESSING SYSTEM

This is a continuation of Ser. No. 532,439 filed Dec. 13, 1974, which was a continuation of Ser. No. 385,153, filed Aug. 2, 1973.

BACKGROUND OF THE INVENTION

It is known in accordance with the teaching in U.S. Pat. No. 1,988,634 to provide a key card having separate conclusions displayed thereon. A plurality of screen cards is adapted to be placed over the key card. Each screen card is provided for a distinguishing characteristic of one or more of the conclusions of the key card and having means thereon for indicating the characteristic. A plurality of openings in each card for exposing those conclusions to which the characteristic applies, and the openings are of different sizes to indicate the certainty, probability and possibility of the presence of the characteristic in the exposed conclusions.

Another known system is disclosed in U.S. Pat. No. 3,186,111 for indexing information which includes a deck that comprises a large number of property cards and a reference card. All of the cards are the same size and shape so that selected groups of cards may be stacked uniformly. All of the property cards are semi-transparent so that a person can easily see through at least two cards in ambient light. Identical coordinate locations on the respective cards are superposable when selected cards are stacked with each of the coordinate locations corresponding to a different item. Each of the property cards is perforated at each coordinate position corresponding to each item with respect to which the property represented by that card is associated. Each of the property cards is perforated in a different pattern of coordinate positions than each of the other property cards, but some of the property cards are perforated in the same positions. Each property card bears a legend identifying the property associated with items represented by perforations in that card. Such a system is known as a "peek-a-boo" retrieval system.

A further retrieval system is covered in U.S. Pat. No. 3,215,848 which is directed to a permanent memory for storing items of information as visual indications. A record contains an item of information in the form of visual indicators. Means is provided for comparing the item on the record with the items stored in the memory, and means derives from each comparison an output signal but only when the extent of the match between the items compared exceeds a given value. Specifically, this patent postulates for each disease the existence of a spectrum of "significances" for each positive symptom (but not negative findings). Said "significance" is entered in a line (or other form) of varying total light transmittance corresponding to the "significance". An overlying patient film recording positive findings is then compared with the master film by aligning the symptom lines of the two films and passing light through the superimposed films. A measure "indicative of the probability that a patient has a particular disease" is said to be obtained by comparing the amount of light which passes through the "two films as compared with the amount of light which would pass through the spectrum of the disease alone."

U.S. Pat. No. 2,795,705 is directed to a system wherein the amount of light detected by a photocell at any given instant is compared with the amount of light that would be obtained if there were actually a mismatch. Thus, since the amount of light detected by the photocell due to mismatch at a single information area will be small compared with the amount of light due to a mismatch, the system can readily detect the difference between the two. This provides greater accuracy in identification of recorded information.

None of these systems is capable of utilizing the pertinent function of the probability of occurrence of findings in a class in comparison with the information regarding an object which is a possible member of the class in the manner of the present invention. It is of note, however, that other systems may be thought of as special cases in this system by the use of appropriate function modification cards, but the statistical models they represent have extremely limited applicability to the real world.

SUMMARY OF THE INVENTION

The present invention relates to a data processing system for comparing stored information which is a function of the probability of occurrence of certain findings in a class or classes with recorded information relating to the actual or presumed occurrence of these certain findings in a particular object or objects. An index of matching is established between the class(es) and the object(s).

The present invention utilizes stored information which is a function of the probability of occurrence of certain findings in a particular class or classes. A record is prepared recording certain findings to provide an object record. The object record is compared with the stored information and an index of matching is established between the stored information and the information of the object record to provide readout information.

An object of the present invention is to provide a data processing system which matches information of probability of occurrence of certain findings with an object record that has recorded thereon certain findings.

Another object of this invention is the provision of a data processing system wherein record means is provided with information representing probabilities of occurrence of certain findings.

A further object of the present invention is to provide a data processing system wherein a plurality of function modification means is provided which modify the recorded information in a readily variable manner corresponding, for example, to various statistical models.

An additional object of this invention is the provision of a data processing system which includes object record means that is prepared by recording certain findings.

A principal object of the invention is to provide a practical means of replacing algorithms with more widely applicable statistical and probabilistic reasoning in many areas.

Another object of the invention is to provide a formal model for probability, statistical, and game theory computations and reasoning.

It is another object of the invention to provide a formal non-digital model for probability, statistical, game theory, information theory, and related computations using graphic rather than digital concepts.

Another object of the invention is to provide a formal method of carrying out the specific inductive reasoning utilized in medicine for the diagnosis of disease and in related areas.

It is another object of the invention to provide a flexible system of performing statistical inferences from both standard distributions and non-standard populations, and of performing formal inductive reasoning in general, such as determining the likelihood distribution of symptoms in a rare disease where few cases have been studied.

It is a further object of this invention to provide a system to utilize such statistical inferences as the likelihood of probabilities for further related probability computations, such as determining the likelihood distribution of probabilities that a new patient has a rare disease for which there have been done only a small number of observations.

It is a further object of this invention to provide a system for determining if an object is a member of two or more classes.

It is still a further object of this invention to provide a system for practical solution of problems in game theory, both of the classic von Neumann type and of the statistical type as they occur in the real world, in decisions for further medical testing or treatment, patient management in accordance with insurance coverage, and evaluation of medical care.

Still another object of the present invention is to provide a data processing system whereby object record means having recorded certain findings is compared with record means having stored information representing probabilities of occurrence of certain findings and readout signals are obtained as a result of such comparison therebetween.

A still further object of this invention is to provide a simple and relatively inexpensive system for providing output information based upon the comparison of probabilities of occurrence of certain findings in a class or classes with findings of fact in a particular object.

It is a further object of the invention to apply optimal statistical and probability techniques to problems of alphanumeric character recognition and pattern identification.

These and other objects, features, and advantages of the invention will be apparent from the following more particular description of the invention as illustrated in the accompanying drawings.

DETAILED DESCRIPTION OF THE INVENTION

The present invention will be described in relation to diagnosing the probability of disease based upon a comparison of the recorded probability of symptoms of diseases with a record made by the patient in answer to pertinent questions regarding his or her health. It is to be understood, however, that the present invention can be used in conjunction with various applications such as in any problem of statistical inductive reasoning, as a portion of pattern, character, and object recognition systems, evaluation of credit risk, stock selection, use at employment agencies, and all other situations where a judgement is to be rendered based upon a preponderance of evidence.

As used here, the term "symptom" refers to a manifestation of a disease such as the presence of abdominal pain, fever, vaginal bleeding, swelling, results of laboratory tests and so on. The probability of the symptom refers to the relative frequency with which that particular symptom occurs in a very large number of cases of the disease. For example, abdominal pain is a common symptom of gastroenteritis, whereas vaginal bleeding is generally found only coincidentally in women of childbearing age with gastroenteritis.

A simplified system is illustrated in FIGS. 1-4 wherein a light source 10 supplies light to a class card 12, a function modification card 14 and an object card 16. Light that passes through these cards in a modified form is concentrated via convexo-convex lens 18 onto sensing means 20 such as a photocell or other suitable light-activated means. The output from sensing means 20 is supplied to output terminal 22 whereat it can be utilized to operate an indicating or recording apparatus or any other means.

Figure 2:
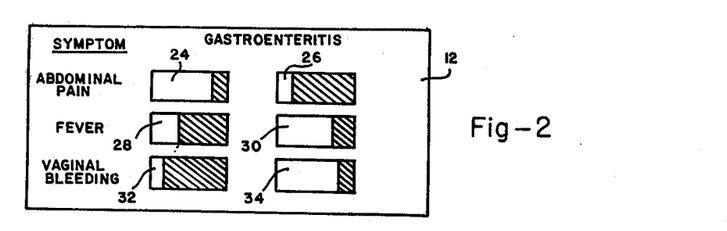
FIG. 2 illustrates a class card having recorded thereon the probabilities of occurrence of certain findings with Table 1 illustrating assumed probabilities or symptoms of gastroenteritis located on the class card.

Class card 12 as shown in FIG. 2 has recorded thereon a certain disease, in this case, gastroenteritis. Three symptoms are listed as abdominal pain, fever, and vaginal bleeding. Openings 24 and 26 are provided in card 12 in alignment with abdominal pain. Opening 24 has 20% of its area shaded so that 80% of the light from light source 10 ca pass therethrough which would mean that in the case of gastroenteritis, there is an 80% probability that a patient will have abdominal pain. Opening 26 has 80% of its area shaded so that only 20% of light will pass therethrough indicating only a 20% probability of freedom from abdominal pain in a patient having gastroenteritis.

Openings 28 and 30 are disposed in class card 12 representing the symptom fever, and openings 32 and 34 are provided in card 12 in alignment with vaginal bleeding. Fever will probably occur 40% of the time in gastroenteritis, whereas it will not occur 60% of the time. A 20% probability of occurence of vaginal bleeding is found in gastroenteritis, whereas 80% of the time it will not occur, as shown by openings 32 and 34. Table 1 next to card 12 sets forth the assumed probabilities of the symptoms of gastroenteritis.

Thus, class card 12 will have stored thereon the probabilities of occurrence of symptoms of a disease. The total probability of occurrence for the presence of each symptom and the absence of each symptom is 100%. While only three symptoms have been recorded on class card 12 in the case of gastroenteritis, more symptoms can, of course, be provided on this card.

Figure 3:
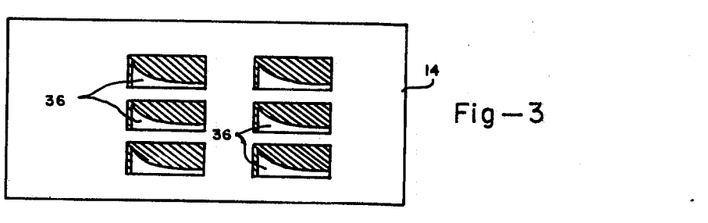
FIG. 3 illustrates a function modification card which modifies the light that is transmitted through the class card.

FIG. 3 illustrates function modification card 14 which is provided with openings 36 therein corresponding to the number of openings 24, 26, 28, 30, 32, and 34 in card 12. Openings 36 have a configuration such that they convert the amount of light transmitted through the respective probability openings 24, 26, 28, 30, 32, and 34 to logarithmic values of their multiples (to avoid dealing with fractions and negative logarithms).

The shape of the openings in the function modification card 14 may vary depending upon the statistical model or probability space which is being represented, and in certain situations, multiple passes of varying function modification cards may be necssary to achieve optimal results.

Figure 4:
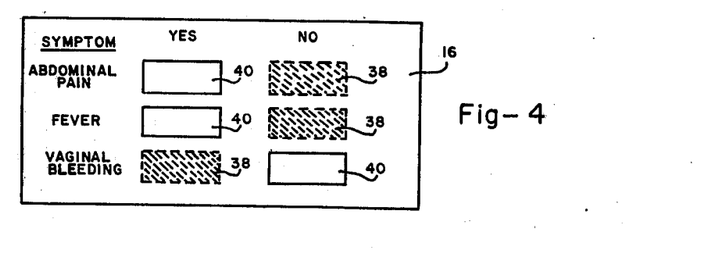
FIG. 4 illustrates an object card that has recorded certain findings based on existing facts.

Object card 16 is illustrated in FIG. 4, and it is prepared by a patient whereby in answer to questions relating to symptoms, the patient punches out perforated areas 40 under "yes" and "no", leaving no openings at 38 therein. This then is a record that has recorded thereon certain facts based on the information supplied by the particular patient.

Figure 1:
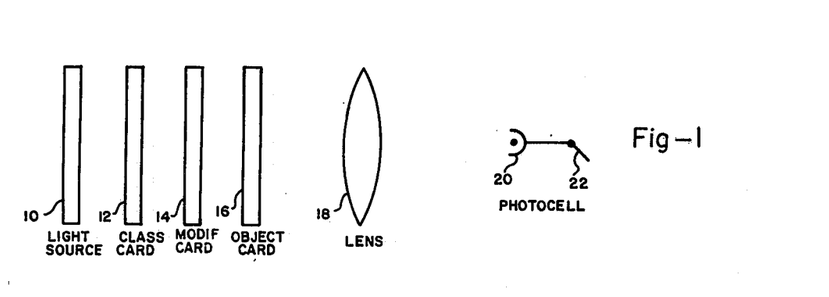
FIG. 1 is a schematic representation of one aspect of the present invention.

In operation, class card 12, function modification card 14 and object card 16 are placed one after each other as shown in FIG. 1 between light source 10 and lens 18. Light from light source 10 is transmitted through probability openings 24, 26, 28, 30, 32, and 34 in accordance with the area of these openings. Openings 36 in function modification card 14 screen out an amount of light from the openings in class card 12 to convert the light passing through openings 24, 26, 28, 30, 32, and 34 representing a multiple of probabilities into the log values thereof and this converted light is then transmitted through openings 40 or blocked by not-punched-out areas 38 of card 16. The light transmitted through openings 40 is converged via lens 18 onto photocell 20 which will provide an output at terminal 22 in accordance with the amount of light received by photocell 20. This will provide output information that can provide a probability of fitting based on the comparison of the information provided on card 16 by the patient with the stored and modified probability of occurrence of symptoms provided by cards 12 and 14 after making certain assumptions and determining similar values of the rest of possible diseases.

Figure 5:
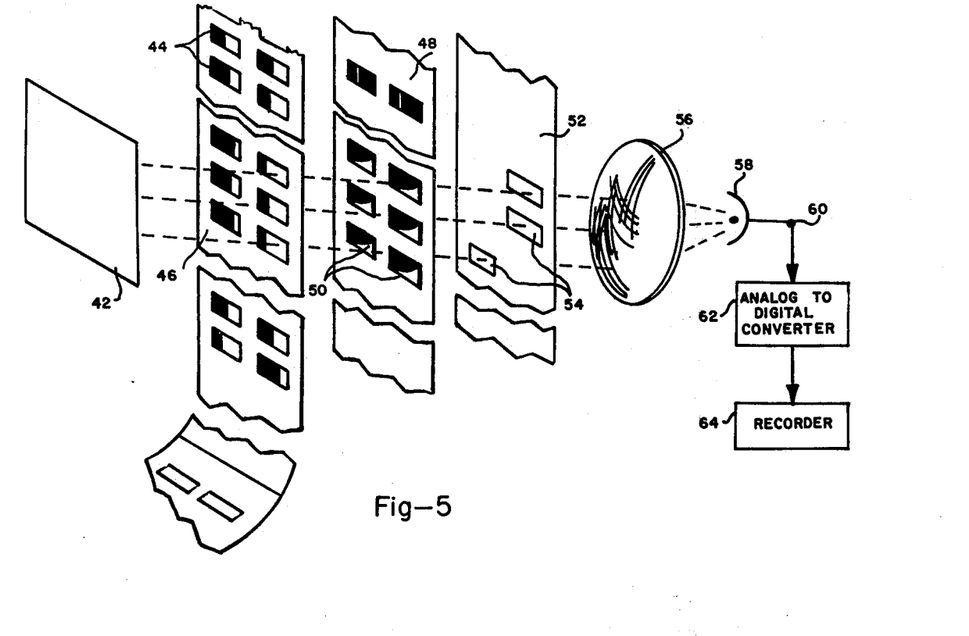
FIG. 5 illustrates in perspective an embodiment of FIG. 1.

FIG. 5 illustrates a modification of the invention wherein light source 42 transmits light through openings 44 which are disposed in alignment in film 46. Openings 44 are similar to openings 24, 26, 28, 30, 32, and 34 in class card 12 of FIG. 2 and the horizontally-aligned openings 44 represent a multiple of the probability of occurrence of symptoms of as many diseases as are desired to be recorded on film 46.

Film 48 is provided with openings 50 in the same manner as openings 36 in function modification card 14 in FIG. 3 in order to modify the amount of light transmitted through corresponding openings 44 into the logarithmic values thereof, or other chosen functions.

Object card 52 is similar to object card 16 of FIG. 4, and it is provided with openings 54 representing "yes" or "no" answers which a patient punches out in answer to questions. The object card 52 can be supplemented by laboratory tests as well as information supplied by the examining physician.

In operation, object card 52 is held stationary in a holder (not shown). Film 46 is driven and stopped sequentially in coincidence with a chosen stationary frame of film 48 and with object card 52, moving by well known film-driving means that need not be shown and described for purposes of simplicity. Light from light sources 42 passes through openings 44 and 50 in films 46 and 48 and through openings 54 whereat this modified light is converged via converging lens 56 onto photocell means 58 and the signal generated by photocell means 58 is provided at output terminal 60 which can be connected to a suitable indicating or storing means to provide an indication or record of the probablity of occurrence of a disease or diseases a patient is likely to have as a result of the information contained on object card 52 in comparison with the stored probability of occurrence of symptoms of disease.

A typical circuit for utilizing the output at output terminal 60 would be conventional analog to digital converter circuit 62 which output therefrom is used to operate recorder 64.

Thus, the system of FIG. 5 will enable determination of a relative fit between an object card prepared by a patient and known information regarding a disease classification.

The output from terminal 60 can provide a graphic write-out on tape, if desired, which is synchronized with the class card feeding reel. The write-out could be, for example, an electrocardiograph machine.

Figure 6:
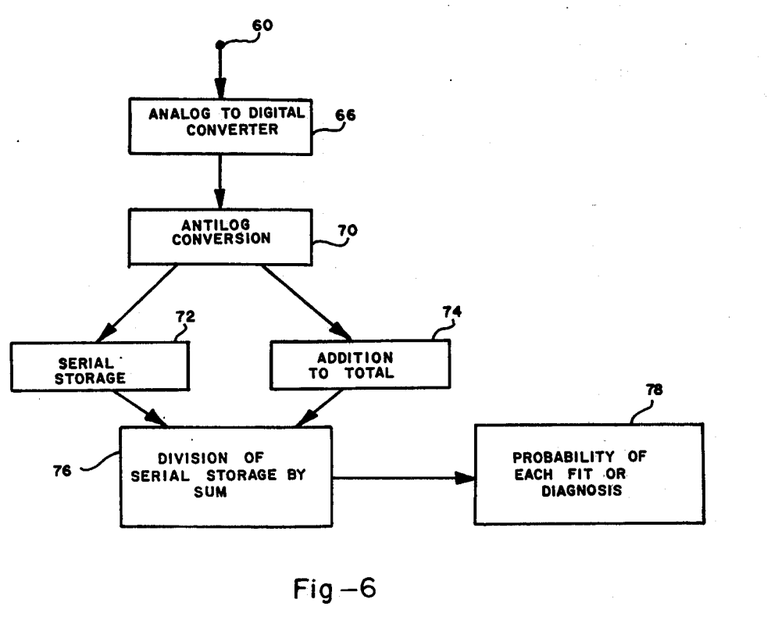
FIG. 6 is a block diagram of an electronic circuit using conventional circuitry to process the information.

FIG. 6 illustrates an alternative system for providing a readout of the probability of diagnosis utilizing conventional electronic circuitry. Output terminal 60 is connected to an analog to digital converter circuit 66 so that the analog signal appearing at output terminal 60 is converted to a digital signal. The digital signal from circuit 66 is supplied to analog conversion circuit 70 and the output therefrom is supplied to serial storage circuit 72 and added to total circuit 74. Outputs from circuits 72 and 74 are supplied to divider circuit 76 wherein the output from circuit 74 is divided into circuit 72. The output from circuit 76 operates circuit 78 which provides a probability of each fit or diagnosis on the basis of certain assumptions including that the class card reel contains all possible diagnoses and the patient has one disease.

When it is considered a priori that the probability of each class may be assigned a value other than unity (some diseases are known to have a greater prevalence than others), then an additional aperture is provided representing the a priori probability of the class (prevalence of the disease).

In some applications, where further processing of the information may be necessary, the output of any of the systems may be recorded on a strip of film or the like using a focused image of the results from an appropriate lens system. The function modification card may be replaced by a lens or mirror system which passes the light in proportion to the chosen function of the expressed data such as, for example, a linear to logarithmic conversion using a Fresnel type lens with log conversion areas instead of focusing concentric circles as in the conventional type of Fresnel lens. Or by use of a light receiver system which performs addition over a period of time, the class card data bars which are overlaid by the appropriate object card are passed over a slit illuminated by a light source which varies in proportion to the chosen function. Or, these cards can be moved at a variable speed past an unvarying lighted slit to achieve a light output to represent the chosen function.

The representation on the class card should be distinguished from the "patient response" or similar data from which it is derived. Ideally, the class card representation corresponds closely to knowable reality, whereas the patient response may be an honest answer subject only to human error, the deliberately misleading responses of a drug addict trying to get drugs from the doctor, or a laboratory determination subject to the usual statistical errors.

A method of managing this type of error in a single response is to represent a positive "patient response" as both a large positive and a small negative response on the object card, with associated probabilities being derived by runs of the object card. Thus a patient response of "yes" would be represented by 90% positive runs with the object card, or 90 positive-response runs of 100. A similar result may be achieved by relative darkening of object card apertures on film, "yes" and "no".

A second method, of course, is to employ repetitions to reduce errors.

A third method, employed elsewhere in this description, is to consider that the error is attributed to the class cards, and the patient responses are taken at their face value, with an associated increased error of the class cards. Of course, the class card statistical methods probably contained errors related to inaccurate classifications because of statistical errors initially during their development. This method is, of course, not applicable in situations (such as drug addict responses and other conditions) where errors do not have ordinary types of statistical distributions. Here, game theory methods to be disclosed would be more generally applicable.

When multiple cards are used to replace a superimposition technique, a sequential exposure or sequential card combination technique may be used.

Figure 7:
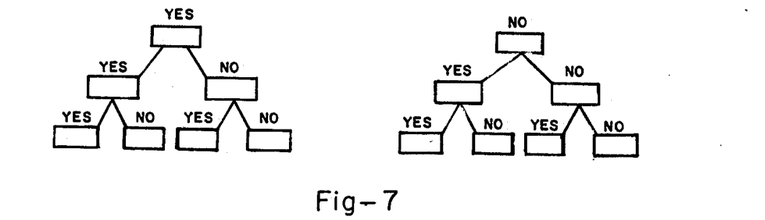
FIG. 7 is a representation of a branching-chain logical method.

A more generally logical method of completion of the object or patient card would be as a branching-chain series of responses as illustrated in FIG. 7. Utiilizing the present invention, the appropriate probability and conversion cards would underlie the possible response apertures.

The method described hereinabove assumed that the probability representations in each row could be represented by a single "yes" or "no" response in that row, which is at best an approximation because the probability values may vary depending upon previous responses. For example, a patient with an elevated rectal temperature will almost certainly also have an elevated oral temperature regardless of the underlying illness that she has, such as appendicitis, tubal pregnancy, or whatever.

Figure 8:
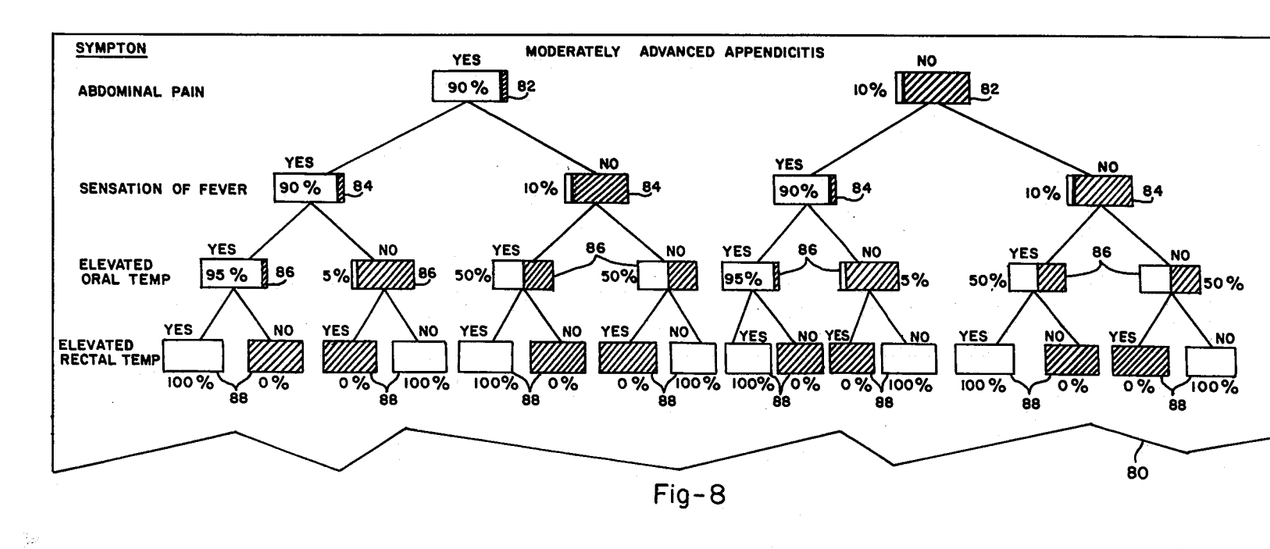
FIG. 8 illustrates a class card utilizing the branching-chain method of FIG. 7.

Fig. 8 illustrates a class card 80 of moderately advanced appendicitis which has recorded thereon under symptoms abdominal pain, sensation of fever, elevated oral temperature, and elevated rectal temperature. Openings 82, 84, 86, and 88 are also disposed in alignment with their respective symptom and each opening is provided with an indication of the percentage of passage of light therethrough. Openings 82, 84, 86, and 88 are also disposed in a branching-chain arrangement which will provide a more realistic probability of occurrence of any of the symptoms than would be obtained without regard to symptom inter-relationships.

The class card 80 of FIG. 8 can be then used in conjunction with a function modification card as illustrated in FIG. 3 and an object card such as shown in FIG. 4 with a light source, lens, and light-sensing means in order to provide a readout or recording of the information as in FIG. 1, or the class cards and function modification cards thereof can be incorporated as frames on film and operated in the manner of the embodiment of FIG. 5.

Figure 9:
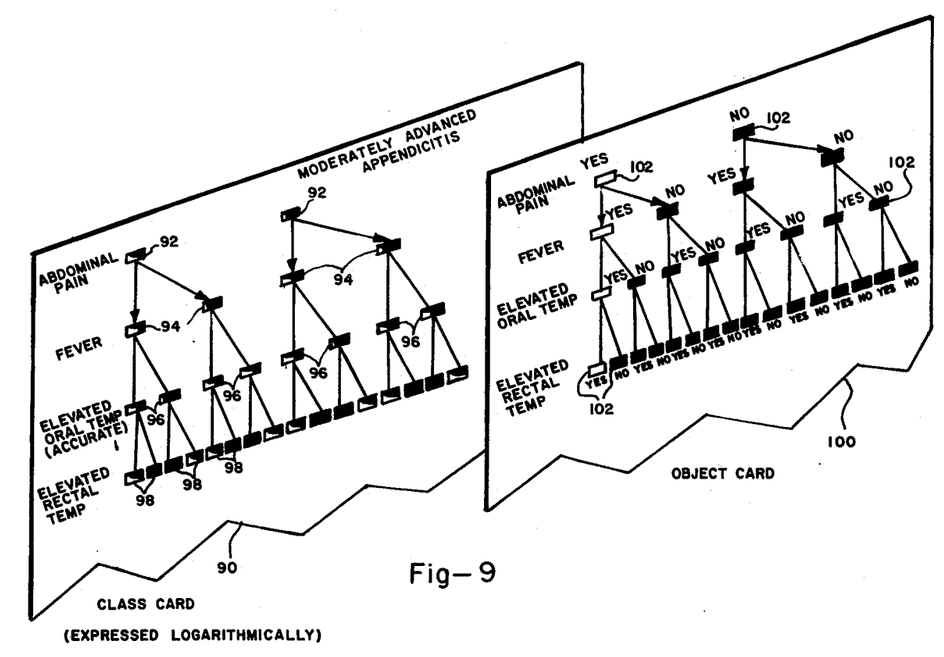
FIG. 9 is a perspective view of a combination (class card and function modification card) and a patient card using the branching-chain method.

FIG. 9 illustrates the branching-chain arrangement as disclosed in FIG. 7 and FIG. 8 with class card 90 openings 92, 94, 96, and 98 in alignment with the respective symptoms expressed logarithmically to permit the passage of light therethrough based on the combination probability of occurrence of a symptom and the logarithmic values of their multiples so that a class card and function modification card are combined as one card 90.

Object card 100 is the same as the object card 16 of FIG. 4 except that the perforated openings 102 to be punched out by the patient are arranged in the branching-chain arrangement. Thus, cards 90 and 100 can be operated as in the manner of FIG. 1 or on frames of film as in FIG. 5.

Figure 10:
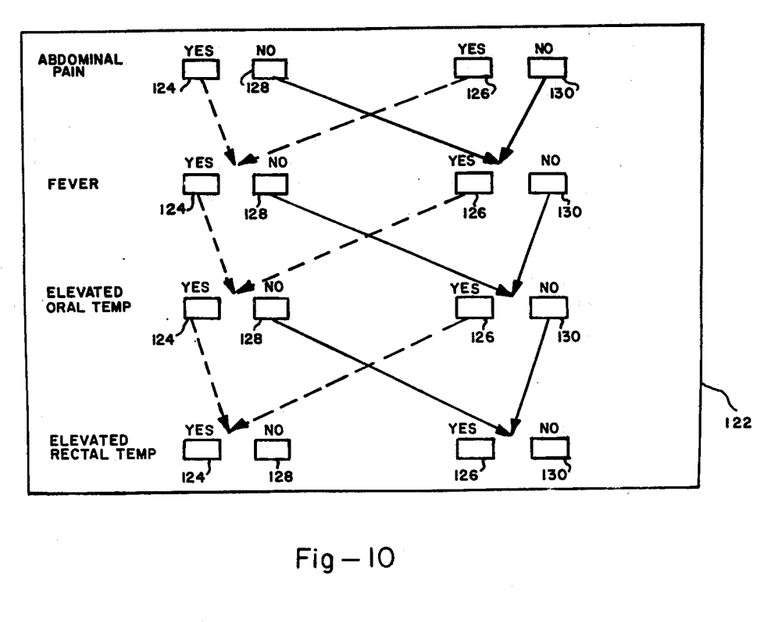
FIG. 10 is a patient questionnaire for use with the Markov type of branching-chain method of probability computation.

FIG. 10 illustrates a specially designed questionnaire constituting a patient card 122 for use in Markov-branching method. As shown, opposite each symptom there are areas 124, 126 under "yes" and areas 128, 130 under "no". The "yes" areas are interconnected by broken lines and the "no" areas are connected by non-broken lines. Thus, if a patient punches out area 124 for abdominal pain, the patient is directed to proceed to the left side of the symptom fever where he punches out area 128. The patient is then directed to proceed to the right hand side for the symptom elevated oral temperature, etc.

Figure 11:
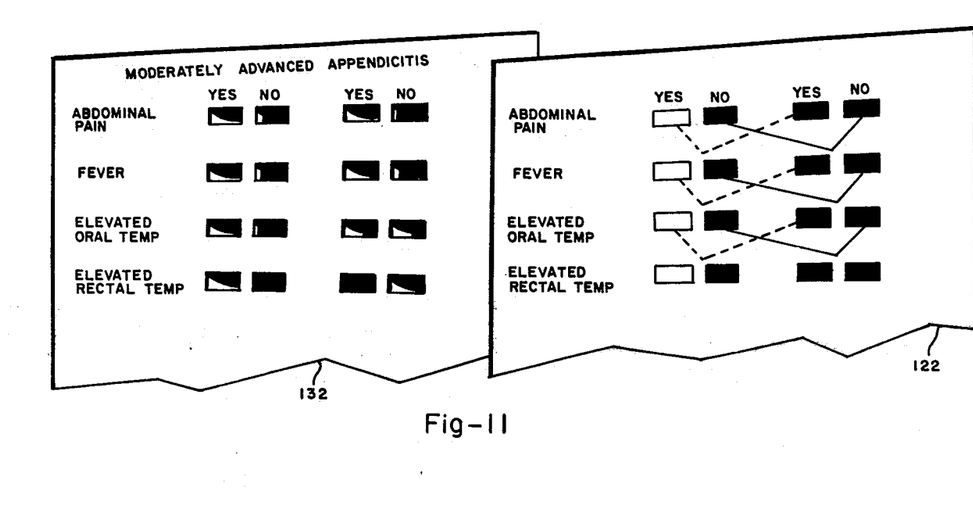
FIG. 11 is a perspective view of a combined class-log modification card to go with the questionnaire of FIG. 10.

After the object or patient card 122 has been completed it is combined with the combined class and function modification card 32 and operated as hereinbefore described to provide a readout of the information. FIG. 11 shows a class card 132 (combined class and function modification card) and the Markov questionnaire 122.

In the present invention, as with any data processing equipment, the problem of accuracy is paramount. Various methods of multiplexing and parity checking are within the scope of the present invention. In order to minimize error, the light transmitting openings may be larger. If the openings are smaller, then the practice of this invention is more limited and less accuracy is attained. The use of the misalignment concept in comparison with the amount of light due to mismatch as taught by U.S. Pat. No. 2,795,705 can be used in conjunction with the present invention to improve accuracy.

One important way to reduce error is to combine the class card and the function modification card as mentioned in conjunction with card 90 of FIG. 9. This constitutes an important feature of the invention.

Figure 12A:
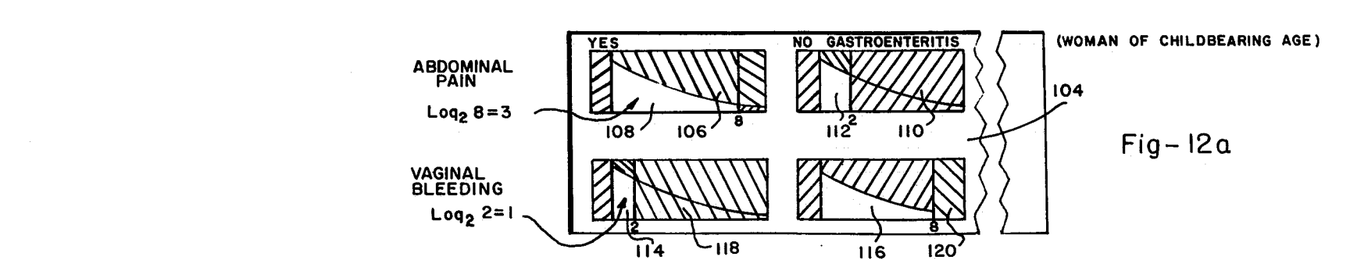
FIGS. 12a, 12b, 12c, and 12d are illustrations of an enlargement method used to increase reliability of the computation to any desired degree.

FIG. 12a illustrates a combined class and function modification card 104 covering gastroenteritis in a woman of child-bearing age. Area 106 opposite the symptom abdominal pain represents the superimposition of a logarithimic conversion upon a probability assumed as 0.8 × 10 that a patient with gastroenteritis will have abdominal pain. If the logarithm is to the base 2, then the logarithmic value is 3 and occupies the open area 108.

In alignment with area 106 is area 110, which is the logarithm to the base 2, thereby providing open area 112. Thus, open areas 108 and 112 in card 104 opposite abdominal pain constitute the total probability of various findings in the disease gastroenteritis with a logarithic function conversion. Open areas 114 and 116 in areas 118 and 120 opposite vaginal bleeding constitute the total probability of such symptoms occuring in gastroenteritis.

Figures 12B, 12C:
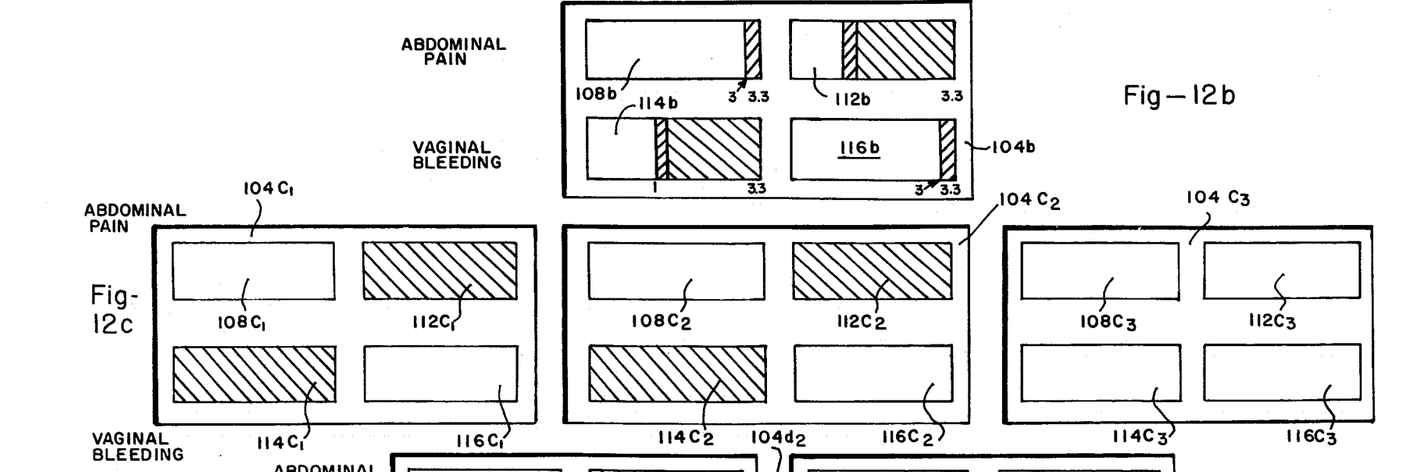
Figure 12D:
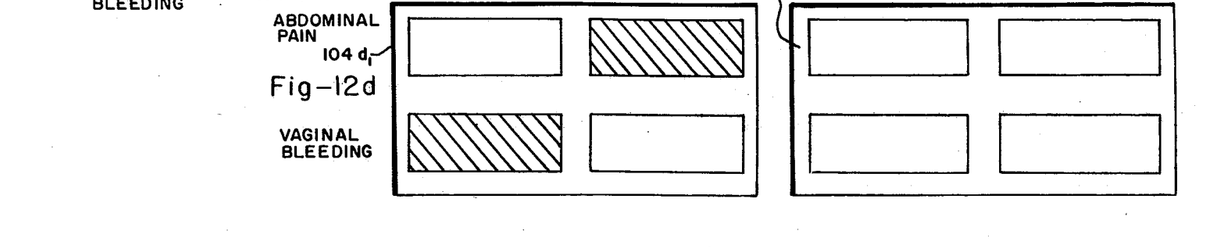

By progressive relative enlargement of the apertures, utilizing additional cards if necessary to contain the relative enlargements, any desired degree of accuracy may be achieved. Such a system of enlargement and use of additional cards is illustrated in FIGS. 12b, 12c, and 12d. Areas 108b, 112b, 114b, and 116b of card 104b of FIG. 12b represent a five-fold enlargement of corresponding areas 108, 112, 114, and 116 of Card 104 of FIG. 12a. FIG. 12c represents a further enlargement of areas 108b, 112b, 114b, and 116b onto three cards 104c(1), 104c(2), 104c(3) wherein areas 108c(1), 108c(2), 108c(3) represent a three-fold enlargement of area 108b of FIG. 12b. This is true of the other areas 112c, 114c, and 116c of FIG. 12c.

FIG. 12d represents cards 104d(1) and 104d(2) wherein the areas therein are binary representations of the multiple areas of the cards of FIG. 12c. By using conventional parity checking techniques, substantially error-free readouts of the information will be achieved.

In order to provide a system with greater accuracy, the system as taught by U.S. Pat. No. 2,795,705 can be utilized in conjunction with the present system so that more accurate readout of the recorded class card and function modification card or combination thereof along with the patient card can be accomplished.

MEMBERSHIP IN TWO OR MORE CLASSES (A PATIENT WITH TWO DISEASES)

Figure 13:
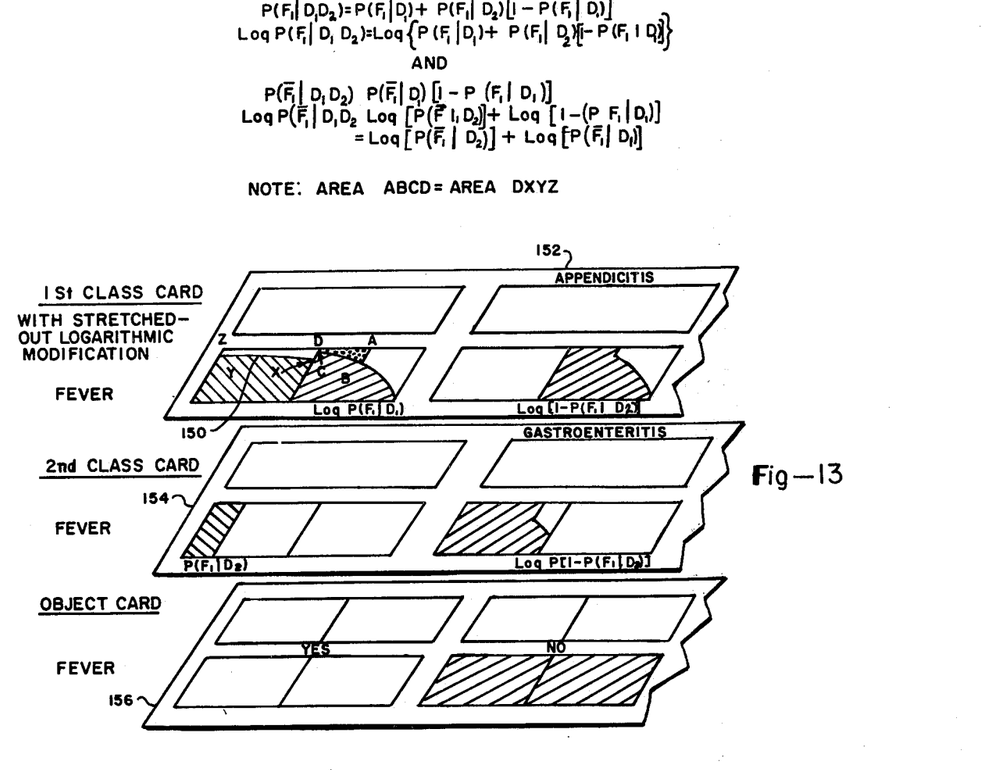
FIG. 13 is an illustration of a method for determining the probability that an object is a member of two classes, assuming that a positive finding is dominant.

The present invention can also be used with reference to the problem of an object which can be a member of two classes or a patient who has two diseases, as shown in FIG. 13. The assumptions underlying this particular approach are used in the manner of expressing a dominance of a positive response over a negative response. Thus, "headache yes" plus "headache no" is read as "headache yes" when combining disease cards.

A feature of this two-class approach in the use of a "stretched-out" logarithmic curve 150 in first class card 152 requiring that the portion of the logarithmic curve which is not exposed by a positive response is stretched out over an adjacent aperture, and the fraction of this that is taken corresponds to the probability of occurrence of the symptom in the second disease or class. In the case of the probability that the finding is absent, then the logarithm of a probability product is the sum of the logarithms of the probabilities. Second class card 154 is formed in the same manner as first class card 152 and object card 156 is similar to class card 16 of FIG. 4. These cards are then processed as described in conjunction with FIGS. 1 and 5 to provide the readout information therefrom.

By using a similar approach or by combining the symptoms of classes (diseases), it is possible to deal with the problem of an object which is a member of more than two classes (a patient who has three or more diseases).

GENERALIZED STATISTICAL INDUCTION AND DEDUCTION

The present invention may also be used for many forms of inductive reasoning and the derivation of estimates of probabilities. Consider the following problem:

There are five identical urns, infinitely large, the first containing all white balls; the second: ten percent black balls, the remainder white; the third: 50% black balls; the fourth: 80% black balls; and the fifth: 100% black balls.

A statistician knowing the above withdraws five balls from an urn and finds that one ball is black, the remaining four white. Required is the calculation of the likelihood that the drawing came from each of the urns, which he does in the following manner:

| Urn | Probabilities as listed: | | | | |
|---|---|---|---|---|---|
| | 1 | 2 | 3 | 4 | 5 |
| black | 0 | .1 | .5 | .8 | 1 |
| white | 1 | .9 | .5 | .2 | 0 |
| white | 1 | .9 | .5 | .2 | 0 |
| white | 1 | .9 | .5 | .2 | 0 |
| white | 1 | .9 | .5 | .2 | 0 |
| product (of each column) | 0 | .0656 | .0312 | .00128 | 0 |
| sum of products = .09808 | | | | | |
| probability (product ÷ sum of products) | 0 | .669 | .318 | .013 | 0 |

Figure 14A:
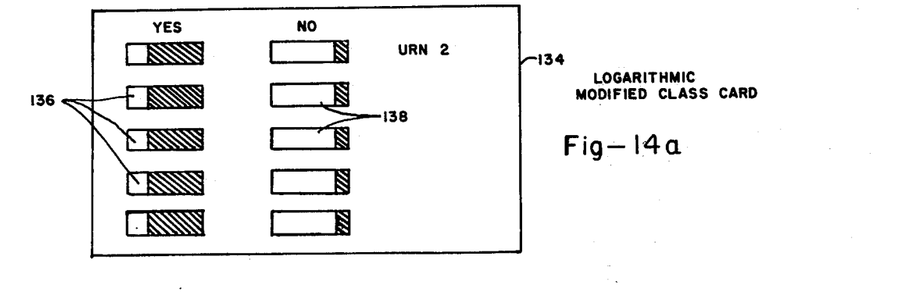
FIGS. 14a and 14b constitute an illustration of a class card (urn 2) and an object card (showing results of a drawing) which are used as part of the computations in an example of inductive reasoning. Somewhat similar reasoning and output might be applied to the induction of the likelihood of probabilities of a new laboratory test in a disease where few cases have been studied.
Figure 14B:
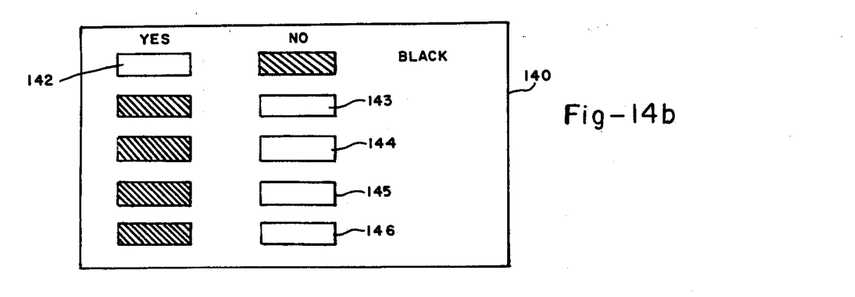

In this invention, each class card would represent an urn. The corresponding probabilities for drawing a black ball from a particular urn would be represented in columns under (black ball drawn) "yes" and "no", as shown by class card 134 in FIG. 14a, wherein areas 136 permit less light to pass therethrough than areas 138. Using appropriate multipliers and conversion factors, a logarithmic modification card would be used. Object card 140 of FIG. 14b would represent a particular result wherein area 142 has been punched out in accordance with a chance selection of a single black ball; and area 143, 144, 145, and 146 in accordance with the chance selection of 4 white balls.

probabilities would then be calculated using the logical processing of FIG. 6.

Many other statistical problems can be solved using this invention, utilizing numerical intervals from zero to one and assuming in most cases probability distributions other than linear as modified by advance knowledge.

Figure 15:
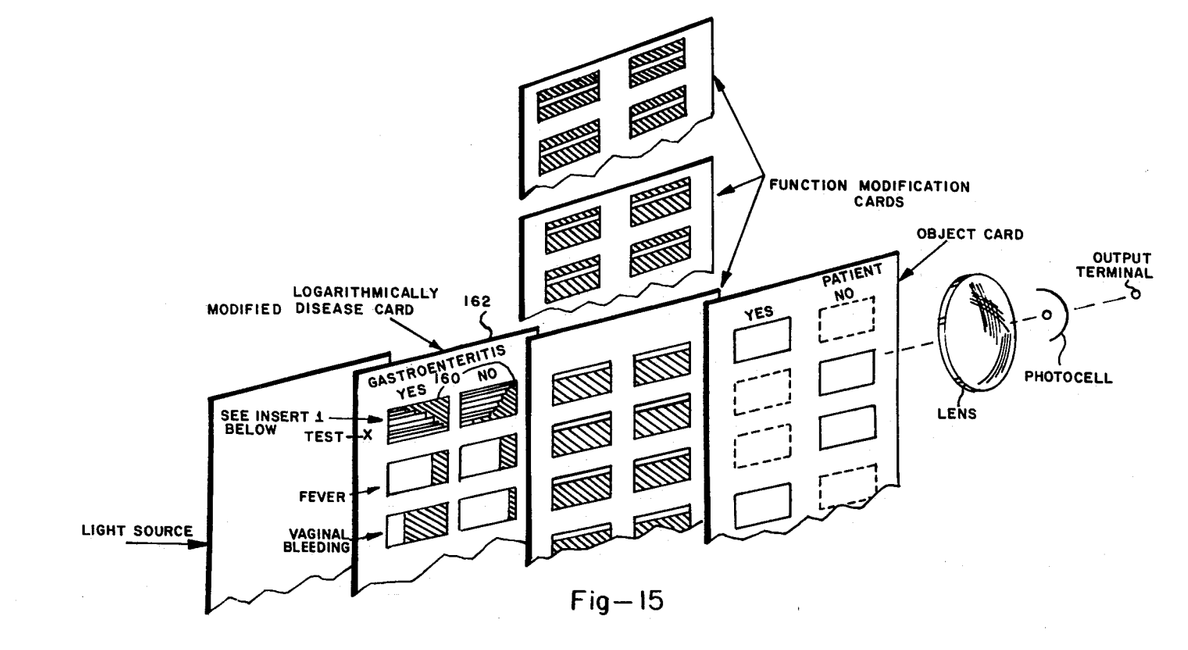
FIG. 15 is an illustration of a method for obtaining likelihood of probabilities output from a likelihood of probabilities input, as in diagnosing an additional suspected case of a disease using a new laboratory test.
Figure 15A:
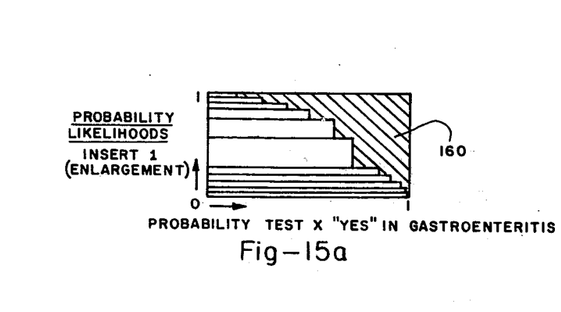
FIG. 15a illustrates enlarged probability likelihoods for use on a class card.
Figure 16:
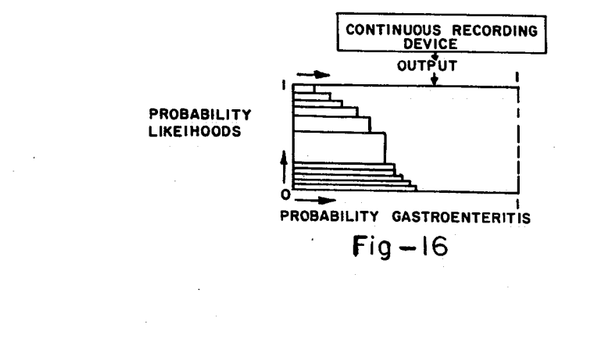
FIG. 16 illustrates a recording of an output from the system of FIG. 15.

Such probability likelihood distributions can be used to replace a single probability entry on a class card and a probability likelihood output can be derived that the object is a member of the class or that the patient has the disease. Such a system utilizing this concept is shown in FIG. 15, with FIG. 15a showing enlarged proability likelihoods 160 that are located on the class card 162. FIG. 16 illustrates a recording of a output that has been provided by using the circuitry of FIG. 6 to a continuous recording device.

USE IN GAME THEORY

In game theory, specifically of the two person type, a pay-off table is constructed representing intersection of the possible moves of the two players. In the present invention, the series of class cards may be thought of as the possible moves of one player and a series of object cards as possible moves of the second player. At coincidence of cards, an amount of light representing an entry in the pay-off table is transmitted.

The same or related cards may also carry information which, as explained in earlier sections, determines the probability of that particular pay-off in statistical games.

A statistical game between a patient (advised by a physician whose interests are assumed identical to his) and nature as an opponent can be utilized. The physician's choice is to perform surgery or not to perform surgery (within a chosen period of time), and "nature's choice" is that the patient has appendicitis or gastroenteritis. The pay-off table assigns utility matters such as cost. Products of probability and pay-off table values may be used as herebefore described in this game theory concept to determine probable pay-off as readouts.

Extensions involve choices of the patient as to further testing (at a certain cost), and other forms of therapy, each choice being represented by different object cards.

CHARACTER OR PICTURE RECOGNITION

Another application of the present invention is that of picture or alphanumeric character identification. Using techniques such as Fourier and Fraunhofer diffraction transformations, the object and class are rendered invariant with respect to spatial orientation and size and the patterns compared using the techniques described heretofore.

The transform may then be scanned in a raster for the presence of dark areas. The actual results of the scan are recorded in an object card (dark: "yes" or "no"). These results on the object card are compared with a series of class cards representing different pictures or characters with appropriate probability information as to the locations of dark spots on a statistical sample of the pictures or characters. An index of matching is established between the object as scanned and the class cards representing each of a series of pictures or characters.

Using proability chains (and combining the results of two scans at right angles), the techniques for identifying an object which is a member of two classes may be used to increase the logical and statistical power of the method.

INFORMATION THEORY

Computations of "Information Bits" from sums of logarithms of probability reciprocals can readily be accomplished by the present invention.

Application of the present invention may generally be utilized sequentially or in series as was described, for example, utilizing the probability output of Generalized Statistical Induction for input for further calculation of likelihood of probabilities in FIG. 15, 15a, and 16.

It should be appreciated that in many applications of the invention utilization of light meters, mechanisms, and the like are unnecessary. The simple sequential stacking of cards over a uniformly illuminated or colored surface (utilizing a superimposed grid for counting when necessary) will enable an unskilled person to draw useful conclusions from complex data.

It will be appreciated by those skilled in the art that many variations may be made in the invention without departing from the underlying principles thereof. It is therefore to be understood that the invention is not limited to the specific forms described but includes other forms within the scope of the appended claims.

The invention is claimed in accordance with the following:

1. A data processing system comprising:
   storage means storing retrievable information in the form of data representing a quantity for each of a plurality of items, said quantities being linearly related and each of which is a measure of the probability of the presence of a respective item within a category and of the probability of the non-presence of said item in said category, the sum of the quantities for each item representing substantially one,
   means for reading out said quantities from said storage means,
   means for converting each of the quantities being read out from the storage means to a logarithmic output,
   means for receiving and adding the converted quantities to provide an output of a value indicative of the logarithm of the product of said quantities, and
   sample means for transmitting to the means for receiving and adding only selected ones of the logrithmic output which correspond respectively to those items probably present in said category and to other items probably not present in said category.

2. A data processing system according to claim 1 wherein the storage means is surface means on which the information is carried in the form of radiation transmitting areas having radiation transmitting properties corresponding to the respective quantity and the means for reading out comprises means for producing radiations to illuminate said areas.

3. A data processing system according to claim 1 wherein the category represents a disease and the items within said category represent symptoms usually associated with said disease, and wherein the items present in the sample means represent a patient's symptoms.

4. A data processing system according to claim 1 wherein a plurality of said storage means is provided, each representing a different category wherein the items and their corresponding probabilities differ from those of another storage means and including,
   means for converting the logarithmic output of each category in a predetermined group to its antilog which represents the product.
   means for adding the antilogs of all the categories within said predetermined group,
   and means for dividing the antilog representing the product corresponding to each category of said group by the sum of the antilogs for obtaining the probability of occurrences of a category in the group.

5. A data processing system according to claim 4 wherein the storage means is surface means on which the information is carried in the form of radiation transmitting areas having radiation transmitting properties corresponding to the respective quantity, the means for converting each of the quantities being read out of the storage means comprising a radiation transmitting area for logarithmically modifying the amount of radiation passing through each of said areas of the storage means.

6. A data processing system according to claim 5, wherein the sample means comprises a surface having radiation transmitting areas for passing only the radiations from selected areas of the storage means.

7. A data processing system according to claim 6, wherein the category represents a disease and the items within said category represent symptoms usually associated with said disease, and wherein the items present in the sample means represent a patient's symptoms.

8. A data processing system comprising:
storage means storing retrievable information representing a quantity related to the probability of the presence of each of a plurality of items within a category and the probability of the non-presence of each of said items in said category, the sum of quantities for each item representing substantially one,
means for reading out said quantities from said storage means,
means for converting the quantities being read out from the storage means to a logarithmic output,
means representing a sample in which at least some of the items are present for inhibiting the read-out from predetermined items not present in said sample and passing the read-out from the remaining items, and
means for receiving and adding all of the converted quantities corresponding to the remaining items, wherein the storage means is surface means on which the information is carried in the form of radiation transmitting areas having radiation transmitting properties corresponding to the respective quantity and the means for reading out comprises means for producing radiations to illuminate said areas, and
the means for converting comprises a radiation transmitting area for logarithmically modifying the amount of radiation passing through each of said areas of the storage means.

9. A data processing system according to claim 8, wherein the means representing a sample comprises a surface having radiation transmitting areas for passing only the radiations from selected areas of the storage means.

10. A data processing system according to claim 8, wherein the source of radiation is a light source.

11. A data processing system comprising,
storage means storing retrievable information in the form of data representing a quantity for each of a plurality of items, each of the quantities being the logrithm of a numerical value representing the probability of the presence of a respective item within a category and the probability of the absence of each such item from said category, the sum of such numbers for each item representing substantially one,
means for receiving and adding logarithmic quantities to provide an output of a value indicative of the logarithm of the product numbers,
and sample means for reading out and transmitting to the means for receiving and adding only selected ones of the logarithmic quantities which correspond respectively to those items probably present in said category and to other items probably not present in said category.

12. A data processing system according to claim 11, wherein the category represents a disease and the items within said category represent symptoms usually associated with said disease and wherein the items present in the sample means represent a patient's symptoms.

13. A data processing system according to claim 11, wherein a plurality of storage means is provided, each representing a different category wherein the probabilities of items differ from those of another storage means and including,
means for converting the output of each category in a predetermined group to its antilog which represents the product,
means for adding the antilogs of all the categories within said predetermined group,
and means for dividing the antilog representing the product corresponding to each category of the group by the sum of the antilogs for obtaining the probability of occurrence of a category in the group.

14. A data processing system according to claim 11 wherein a plurality of storage means is provided, each storing retrievable information representing a quantity related to the probability of the presence and of the absence of each of a plurality of items within a separate category and including,
means for converting the output of a category in a predetermined group to its antilog which represents the product,
means for adding the antilogs of all the categories within said predetermined group,
and means for dividing the antilog representing the product corresponding to each category by the sum of the antilogs for obtaining the probability of occurrence of a category in the group, wherein the storage means is a surface means on which the information is carried in the form of radiation transmitting areas having transmitting properties corresponding to the respective logarithmic quantity and the means for reading out comprises means for producing radiations to illuminate said area.

15. A data processing system according to claim 14, wherein the sample means comprises a surface having radiation transmitting areas for passing only the radiations from selected areas of the storage means.

16. A data processing system according to claim 15, wherein the category represents a disease and the items within said category represent symptoms usually associated with said disease, and wherein the items present in the sample means represent a patient's symptoms.

17. A data processing system according to claim 11, wherein the storage means is a surface means on which the information is carried in the form of radiation transmitting areas having transmitting properties corresponding to the respective logarithm of the quantity, and the means for reading out includes means for producing radiations to illuminate said areas.

18. A data processing system according to claim 17 wherein the sample comprises a surface having radiation transmitting areas for passing only the radiations from selected areas of the storage means.

19. A data processing system according to claim 18, wherein the source of radiation is a light source.

20. A storage processing system according to claim 18, wherein the category represents a disease and the items within said category represent symptoms usually associated with said disease and wherein the items present in the sample means represent a patient's symptoms.

21. A data processing system for processing recorded information comprising:
- class card means having recorded thereon the probability of occurrence of certain findings in a class which comprises openings in alignment with each finding representing the total probability of occurrence thereof;
- logarithmic modification card means having recorded thereon openings in correspondence with said class card openings which modify radiations which pass through each opening to functional values of probabilities'
- object card means having areas in correspondence with said class card and function modification card openings which are adapted to be rendered lucent to said radiations;
- means for aligning said card means,
- means for producing radiant energy and transmitting said energy through said openings, the amount of energy being transmitted through aid aligned openings depending on the transmittance of each of the aligned openings; and
- sensing means for sensing the amount of energy being transmitted through the aligned openings.

22. A data processing system according to claim 21 wherein said class card, said function modification card, and said object card define a branching-chain configuration of FIGS. 8-10.

23. A data processing system comprising:
- storage means storing retrievable information representing a plurality of quantities, each of which is a measure of the probability of the presence of an item within a category and of the probability of the non-presence of a respective item in said category, the sum of the quantities for each item representing substantially one,
- means for reading out said quantities from said storage means,
- means for converting each of the quantities being read out from the storage means to a logarithmic output,
- means representing a sample in which at least some of the items are present for passing only those quantities from the output corresponding to the items present in the sample and those quantities from the output corresponding to those items not present in said sample, and
- means for receiving and adding all of the converted quantities thus passed to provide a single output of a value indicative of the logarithm of the product of said quantities, wherein the storage means is surface means on which the information is carried in the form of radiation transmitting areas having radiation transmitting properties corresponding to the respective quantities and the means for reading out comprises means for producing radiations to illuminate said areas wherein the means for converting comprises a radiation transmitting area for logarithmically modifying the amount of radiation passing through each of said areas of the storage means.

24. A data processing system according to claim 23, wherein the means representing a sample comprises a surface having radiation transmitting areas for passing only the radiations from selected areas of the storage means.

25. A data processing system according to claim 23, wherein the source of radiation is a light source.

26. A data processing system according to claim 23, wherein the category represents a disease and the items within said category represent symptoms usually associated with said disease and wherein the items present in the sample represent a patient's symptoms.

* * * * *